(12) United States Patent
Venkatesan et al.

(10) Patent No.: US 6,939,870 B2
(45) Date of Patent: Sep. 6, 2005

(54) SUBSTITUTED-3-INDOLYL-4-PIPERIDINO-ALKYL HETEROCYCLES FOR THE TREATMENT OF DEPRESSION

(75) Inventors: Aranapakam M. Venkatesan, Rego Park, NY (US); Jamie M. Davis, Ann Arbor, MI (US); Yansong Gu, Pearl River, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/652,424

(22) Filed: Aug. 29, 2003

(65) Prior Publication Data

US 2004/0204402 A1 Oct. 14, 2004

Related U.S. Application Data

(60) Provisional application No. 60/408,376, filed on Sep. 5, 2002.

(51) Int. Cl.[7] .................. C07D 417/14; C07D 403/14; A61K 31/53; A61K 31/549; A61P 25/24

(52) U.S. Cl. .................. 514/223.2; 544/48; 544/183; 544/287; 514/243; 514/266.22; 546/120

(58) Field of Search .................. 544/48, 183, 287; 514/223.2, 243, 266.22

(56) References Cited

FOREIGN PATENT DOCUMENTS

EP          6 662 58 A1       8/1995

OTHER PUBLICATIONS

Abdulqader, A., et al., "Design, synthesis, and pharmacological activities of 2–substituted 4–phenylquinolines as potential antidepressant drugs," *J. Med. Chem.*, 1985, 28, 1394–1398.

Arborelius, L., et al., "5–HT$_{1A}$ receptor antagonists increase the activity of serotonergic cells in the dorsal raphe nucleus in rats treated acutely or chronically with citalopram," *Naunyn–Schmiedeberg's Arch Pharmacol.*, 1995, 352, 157–165.

Armarego, W.L.F., "Improved preparation of phthalazine and quinazoline," *J. Appl. Chem.*, Feb. 1961, 11, 70–72.

Artigas, F., et al., "Pindolol induces a rapid improvement of depressed patients treated with serotonin reuptake inhibitors," *Arch Gen Psychiatry*, Mar. 1994, 51, 248–251.

Cheetham, S.C., et al., "[$^3$H]paroxetine binding in rat frontal cortex strongly correlates with [$^3$H]5–HT uptake: effect of administration of various anti–depressant treaments," *Neuropharmacol.*, 1993, 32(8), 737–743.

Cheng, Y.–C., et al., "Relationship between the inhibition constant ($K_1$) and the concentration of inhibitor which causes 50 per cent inhibition ($I_{50}$) of an enzymatic reaction," *Biochem. Pharmacol.*, 1973, 22, 3099–3108.

(Continued)

Primary Examiner—Mark L. Berch
Assistant Examiner—Kahsay Habte
(74) Attorney, Agent, or Firm—Woodcock Washburn LLP

(57) ABSTRACT

A compound represented by the formula I:

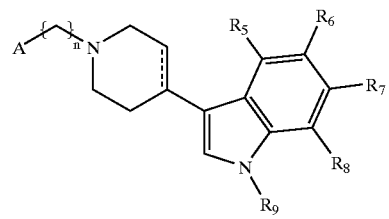

wherein A represents the following heterocycles:

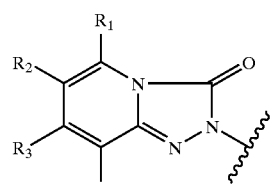

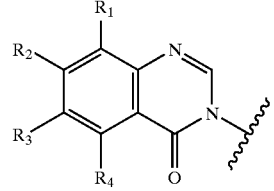

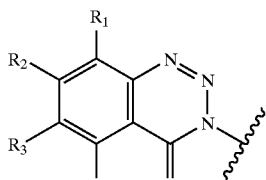

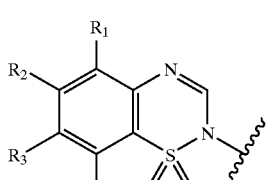

and $R_{1-9}$ are as defined herein, a composition containing this compound and methods for treating disorders of the serotonin-affected neurological systems utilizing such a compound or composition.

5 Claims, No Drawings

OTHER PUBLICATIONS

Hall, M.D., et al., "[$^3$H] 8–hydroxy–2–(Di–n–propylamino)tetralin binding to pre- and postsynaptic 5–hydroxytryptamine sites in various regions of the rat brain," *J. Neurochem.*, 1985, 44(6), 1685–1696.

Invernizzi, R., et al., "Chronic treatment with citalopram facilitates the effect of a challenge dose on cortical serotonin output: role of presynaptic 5–HT$_{1A}$ receptors," *Eur. J. Pharmaco.*, 1994, 260, 243–246.

Kobylecki, R.J., et al., Advances in Heterocyclic Chemistry, *Academic Press*, 1976 Katritzky, A.R., et al. (Eds.), 19, 215–277.

Lazareno, S., et al., "Pharmacological characterization of acetylcholine–stimulated [$^{35}$S]–GTPγS binding mediated by human muscarinic m1–m4 receptors: antagonist studies," *Br. J. Pharmacol.*, 1993, 109, 1120–1127.

Malleron, J.–L., et al., "New indole derivatives as potent and selective serotonin uptake inhibitors," *J. Med. Chem.*, 1993, 36, 1194–1202.

Wustrow, D.J., et al., "3–[[(4–Aryl–1–piperazinyl)alkyl]cyclohexyl]–1H–indoles as dopamine D2 partial agonists and autoreceptor agonists," *J. Med. Chem.*, 1997, 40, 250–259.

SUBSTITUTED-3-INDOLYL-4-PIPERIDINO-ALKYL HETEROCYCLES FOR THE TREATMENT OF DEPRESSION

This application claims the benefit of U.S. Provisional Application No. 60/408,376 filed Sep. 5, 2002.

BACKGROUND OF INVENTION

Pharmaceuticals which enhance serotonergic neurotransmission are useful for the treatment of many psychiatric disorders, including depression and anxiety. The first generation of non-selective serotonin-affecting drugs operated through a variety of physiological functions which endowed them with several side effect liabilities. The more currently prescribed drugs, the selective serotonin reuptake inhibitors (SSRIs), act predominately by inhibiting 5-HT, which is released at the synapses, from being actively removed from the synaptic cleft via a presynaptic serotonin transport carrier.

SSRI's currently available suffers from a serious drawback in that several weeks of treatment is necessary to produce the therapeutic effect. The delayed onset of action is a significant problem, especially in the treatment of patients with severe depression.

It has been shown by Arborelius et.al (Arborelius, L. et al., Naunyn-Schmiedeberg's Arch. Pharmacol. 1995, 352, 157) that acute administration of SSRI's reduces firing of 5-HT neurons of dorsal raphe nucleus in the rodent brain and sustained treatment of SSRI's leads to normalization of the firing activity of the 5-HT neurons. Further more it has been shown by others that the recovery of firing activity of 5-HT neurons is linked to desentization of somatodendritic 5-HT$_{1A}$ autoreceptors. (Invernizzi, R. et al, Eur. J. Pharmacol. 1994, 260, 243.) Hence it has been suggested that simultaneous administration of SSRI's and a 5-HT$_{1A}$ receptor antagonist would lead to rapid onset of antidepressive effect. (Artigas, F. et al, Trends Neurosci. 1996, 19, 378).

Jean-Luc Malleron et. al (Jean-Luc Malleron et. al J. Med. Chem. 1993, 36, 1194) published a series of naphthalene-sultam derivatives of formula 1 as selective serotonin uptake inhibitors, but nothing has been mentioned about the 5HT-1A activity. In the same paper the naphthalene sultam was replaced by different heterocycles such as 2 to 7. These compounds were evaluated for serotonin uptake inhibiton.

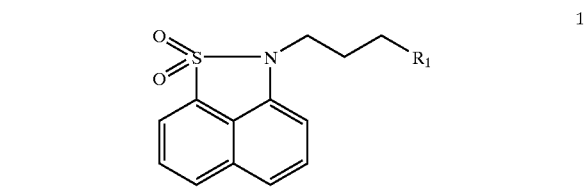

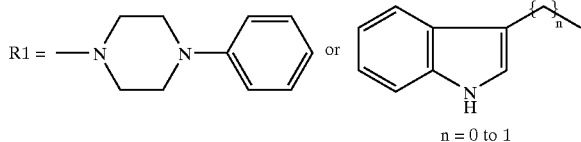

n = 0 to 1

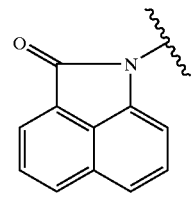

2

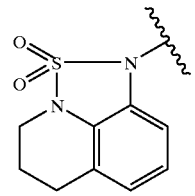

3

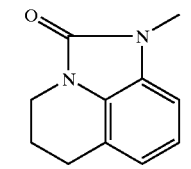

4

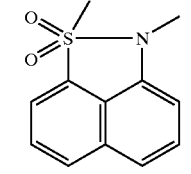

5

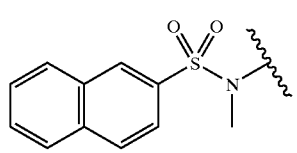

6

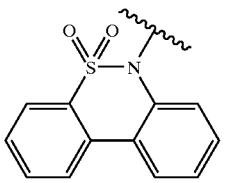

7

Wustrow et al. have disclosed a series of 3-[[4-aryl-1-piperazinyl)alkyl]cyclohexyl]-1H-indoles as dopamine D$_2$ partial agonists in *J. Med. Chem.* 1997, 40, 250.

Cipollina et al. have disclosed a series of indolylcloalkylamines as serotonergic vasoconstrictors for the treatment of vascular or migraine headaches in European Patent Application EP 666258.

SUMMARY OF THE INVENTION

The present invention comprises a compound represented by the formula I:

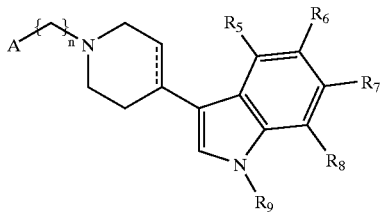

wherein A represents the following heterocycles:

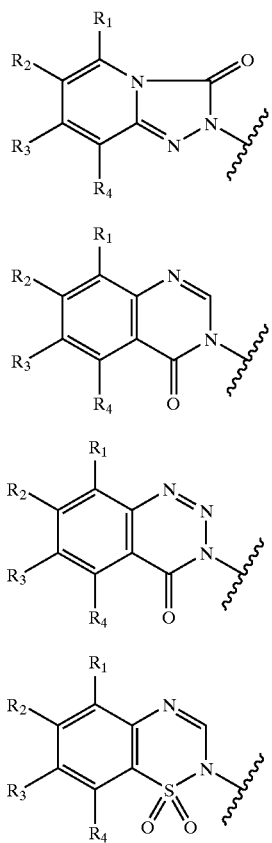

$R_1$, $R_2$, $R_3$, $R_4$, $R_5$, $R_6$, $R_7$ and $R_8$ are independently, hydrogen, straight chain alkyls of 1 to 4 carbon atoms, branched alkyls of 3 to 6 carbon atoms or cycloalkyls of 3 to 10 carbon atoms, halogens such as F, Cl, Br and I, alkoxy group of 1 to 4 carbon atoms, heteroaryloxy, cycloalkoxy (where the cyclic moiety is 3 to 6 membered cyclic system with or with out heteroatom such as O, S, N—$R_9$, hydroxy, nitro, nitrile, amino, carboxy, alkoxycarbonyl of 1 to 4 carbon atoms, alkylcarbonyl of 1 to 4 carbon atoms, aminocarbonyl and alkylaminocarbonyl of 1 to 12 carbon atoms, C1 to C4 fluorinated alkyl (straight and branched), aryl, aryloxy, alkylaryl of C-7 to C-12 carbon atoms, heteroaryl, saturated cycloalkyl with or with out any hetero atom such as N, N—$R_9$, O and S;

$R_9$ is $C_1$–$C_6$ alkyl optionally substituted with $R_{10}$, $C_3$–$C_6$ alkenyl with the proviso that the carbon bearing the double bond is not bonded directly to the heteroatoms such as O,S or N—$R_9$ optionally substituted with $R_{10}$, $C_3$–$C_6$ alkynyl with the proviso that the carbon bearing the triple bond is not bonded directly to the heteroatoms such as O, S or N—$R_9$ optionally substituted with $R_{10}$, $C_6$–$C_{10}$ aryl optionally substituted with $R_{10}$, $C_7$–$C_{10}$ alkyl aryl optionally substituted with $R_{10}$, heteroaryl optionally substituted with $R_{10}$, alkyl heteroaryl optionally substituted with $R_{10}$, $SO_2$-aryl, or $SO_2$-alkyl;

n is 2 to 4;

$R_{10}$ is halogen, nitrile, alkoxy, aryloxy, aryl, heteroaryl, cycloalkyl with or with a hetero atom such as N, O or S;

and all crystalline forms or a pharmaceutically acceptable salt thereof.

The present invention relates to a new class of molecules that have the ability to act at the 5-HT-1A receptor as well as serotonin uptake inhibitors. Such compounds are therefore potentially useful for the treatment of depression as well as other serotonin disorders.

DESCRIPTION OF THE INVENTION

The present invention relates to compounds containing a heterocycle group (8 to 11) connected to a 3-piperidino indole derivative via —$(CH_2)_n$—, where n=2 to 4, and derivatives having pharmacological activity, and to their use in the treatment of diseases affected by disorders of the serotonin affected neurological systems, such as depression and anxiety.

In accordance with this invention there, is provided a group of compounds represented by the formula I, as defined above.

Alkyl, whether used alone or as part of another group includes straight and branched chain alkyl groups containing from 1 to 4 carbon atoms. For example, methyl, ethyl, propyl, isopropyl, butyl, i-butyl and t-butyl are encompassed by the term alkyl. In some embodiments of the present invention alkyl may refer to substituted or unsubstituted alkyl. Carbon number refers to carbon backbone and does not include carbon atoms of substituents such as alkoxy substitutions and the like.

Halogen, as used herein means chlorine, bromine, iodine and fluorine.

Aryl, as used herein refers to single or multiple 4 to 10 membered aromatic ring radicals including but not limited to phenyl, benzyl, naphthalene, indene and indacene. Preferred are phenyl, benzyl and naphthalene. In some embodiments of the present invention, the aryl group may be substituted by $R_{10}$, which is defined as above.

Heteroaryl as used herein refers to single or multiple 4 to 10 membered aromatic ring radicals having from 1 to 3 heteroatoms selected from S, O or N including, but not limited to, furan, thiophene, pyrrole, imidazole, oxazole, thiazole, isoxazole, pyrazole, isothiazole, oxadiazole, triazole, thiadiazole, quinolizine, quinoline, isoquinoline, cinnoline, phthalazine, quinazoline, quinoxaline, napthyridine, pteridine, pyridine, pyrazine, pyrimidine, pyridazine, pyran, triazine, indole, isoindole, indazole, indolizine, and isobenzofuran. Preferred heteroaryls include furan, thiophene, pyrrole, imidazole, oxazole, thiazole, isoxazole, pyrazole, isoxazole, isothiazole, oxadiazole, triazole, thiadiazole, quinolizine, quinoline, and isoquinoline. More preferred heteroaryls include furan, thiophene, imidazole, isoxazole, quinoline, pyridine and pyrazole. In some embodiments of the present invention, the heteroaryl group is substituted.

Preferably, the substituted aryl group is substituted with from 1 to 3 groups. The substituted heteroaryl group is preferably substituted with 1 to 3 groups and more preferably 1 to 2 groups. Alkyl and cycloalkyl groups may also be substituted. Suitable substitutions include, but are not limited to halogen, alkyl, alkoxy, haloalkyl, haloalkoxy, hydroxy, nitro, nitrile, amino, cyano, carboxy, alkoxycarbonyl, alkylcarbonyl, alkoxycarbonylalkyl and alkylcarbonyloxy.

Highly preferred embodiments of the present invention include:

3-[2-(4-(1H-indol-3-yl)-3,6-dihydro-1(2H)-pyridinyl) ethyl]-6-7-dimethoxy-4(3H)-quinazolinone or a pharmaceutically acceptable salt thereof;

3-[2-(4-(1H-indol-3-yl)-1-piperidinyl)ethyl]-6-7-dimethoxy-4(3H)-quinazolinone or a pharmaceutically acceptable salt thereof;

3-[2-(4-(5-fluoro-1H-indol-3-yl)-3,6-dihydro-1(2H)-pyridinyl)ethyl]-6-7-dimethoxy-4(3H)-quinazolinone or a pharmaceutically acceptable salt thereof;

3-[4-(4-(1H-indol-3-yl)-3,6-dihydro-1(2H)-pyridinyl) butyl]-6-7-dimethoxy-4(3H)-quinazolinone or a pharmaceutically acceptable salt thereof;

3-[4-(4-(1H-indol-3-yl)-1-piperdinyl)butyl]-6-7-dimethoxy-4(3H)-quinazolinone or a pharmaceutically acceptable salt thereof;

3-[3-(4-(1H-indol-3-yl)-3,6-dihydro-1(2H)-pyridinyl) propyl]-6-7-dimethoxy-4(3H)-quinazolinone or a pharmaceutically acceptable salt thereof;

3-[3-(4-(1H-indol-3-yl)-1-piperidinyl)propyl]-6-7-dimethoxy-4(3H)-quinazolinone or a pharmaceutically acceptable salt thereof;

3-[3-(4-(5-fluoro-1H-indol-3-yl)-3,6-dihydro-1(2H)-pyridinyl)propyl]-6-7-dimethoxy-4(3H)-quinazolinone or a pharmaceutically acceptable salt thereof;

8-bromo-6-chloro-3-[3-(4-(5-(1H-indol-3-yl)-3,6-dihydro-1 (2H)-pyridinyl)propyl]-4(3H)-quinazolinone}-quinoline or a pharmaceutically acceptable salt thereof;

6-Chloro-3-[3-(4-(1H-indol-3-yl)-3,6-dihydro-1(2H)-pyridinyl)propyl]-4(3H)-quinazolinone or a pharmaceutically acceptable salt thereof;

6-Chloro-3-[2-(4-(1H-indol-3-yl)-piperidinyl)propyl]-4 (3H)-quinazolinone or a pharmaceutically acceptable salt thereof;

3-[2-(4-(1H-indol-3-yl)-3,6-dihydro-1(2H)-pyridinyl) ethyl]-4(3H)-quinazolinone or a pharmaceutically acceptable salt thereof;

3-[2-(4-(1H-indol-3-yl)-1-piperidinyl)ethyl]-4(3H)-quinazolinone or a pharmaceutically acceptable salt thereof;

3-[2-(4-(1-methyl-1H-indol-3-yl)-1-piperidinyl)ethyl]-4-(3H)-quinazolinone or a pharmaceutically acceptable salt thereof;

6-Fluoro-3-[2-(4-(1H-indol-3-yl)-3,6-dihydro-1(2H)-pyridinyl)ethyl]-4(3H)-quinazolinone or a pharmaceutically acceptable salt thereof;

3-[2-(4-(1H-indol-3-yl)-3,6-dihydro-1(2H)-pyridinyl) ethyl]-1,2,3-benzotriazin-4(3H)-one or a pharmaceutically acceptable salt thereof;

3-[2-(4-(1H-indol-3-yl)-1-piperidinyl)ethyl]-1,2,3-benzotriazin-4(3H)-one or a pharmaceutically acceptable salt thereof;

3-[2-(4-(1-methyl-1H-indol-3-yl)-1-piperidinyl)ethyl]-1,2, 3-benzotriazin-4(3H)-one or a pharmaceutically acceptable salt thereof;

3-[2-(4-(1H-indol-3-yl)-3,6-dihydro-1(2H)-pyridinyl) propyl]-1,2,3-benzotriazin-4(3H)-one or a pharmaceutically acceptable salt thereof;

3-[2-{4-(1H-indol-3-yl)-1-piperidinyl)propyl]-1,2,3-benzotriazin-4(3H)-one or a pharmaceutically acceptable salt thereof;

3-[2-(4-(1-methyl-1H-indol-3-yl)-1-piperidinyl)propyl]-1,2, 3-benzotriazin-4(3H)-one or a pharmaceutically acceptable salt thereof;

2-{3-[4-(1H-Indol-3-yl)-3,6-dihydro-2H-pyridin-1-yl]-propyl}-2H-[1,2,4]triazolo[4,3-a]pyridin-3-one or a pharmaceutically acceptable salts there of;

2-{3-[4-(1H-Indol-3-yl)-piperidin-1-yl]-propyl}-2H-[1,2,4] triazolo[4,3-a]pyridin-3-one or a pharmaceutically acceptable salts there of;

2-{2-[4-(1H-Indol-3-yl)-3,6-dihydro-2H-pyridin-1-yl]-ethyl}-2H-[1,2,4]triazolo[4,3-a]pyridin-3-one or a pharmaceutically acceptable salts there of;

2-{2-[4-(1H-Indol-3-yl)-piperidin-1-yl]-ethyl}-2H-[1,2,4] triazolo[4,3-a]pyridin-3-one or a pharmaceutically acceptable salts there of;

2-{4-[4-(1H-Indol-3-yl)-3,6-dihydro-2H-pyridin-1-yl]-butyl}-2H-[1,2,4]triazolo[4,3-a]pyridin-3-one or a pharmaceutically acceptable salts there of;

It is understood that the definition of the compounds of formula I, when $R_1$, $R_2$ or $R_3$ contain asymmetric carbons, encompasses all possible stereoisomers and mixtures thereof which possess the activity discussed below. In particular, it encompasses racemic modifications and any optical isomers which possess the indicated activity. Optical isomers may be obtained in pure form by standard separation techniques.

Pharmaceutically acceptable salts are those derived from such organic and inorganic acids as: lactic, citric, acetic, tartaric, succinic, maleic, malonic, oxalic, fumaric, hydrochloric, hydrobromic, phosphoric, nitric, sulfuric, methanesulfonic, and similarly known acceptable acids. Where $R_1$, $R_2$ or $R_4$ contain a carboxyl group, salts of the compounds of this invention may be formed with bases such as alkali metals (Na, K, Li) or the alkaline earth metals (Ca or Mg).

The compounds of this invention have been found to have affinity for the 5-HT reuptake transporter. They are, therefore, useful in the treatment of diseases affected by disorders of the serotonin affected neurological systems, such as depression and anxiety.

The present invention includes a pharmaceutical composition which comprises a compound of this invention in combination or association with a pharmaceutically acceptable carrier. The composition preferably is adapted for oral or subcutaneous administration. However, it may be adapted for other modes of administration.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents.

The present invention further provides a compound of the invention for use as an active therapeutic substance. Compounds of formula (I) are of particular use in the treatment of diseases affected by disorders of the serotonin.

The present invention further provides a method of treating depression and anxiety in mammals including man, which comprises administering to the afflicted mammal an effective amount of a compound or a pharmaceutical composition of the invention.

The present invention provides a process for the preparation of a compound of general formula I. The core heterocycles 8, 9, 10 and 11 were prepared by the well established literature procedure. (Advances in Heterocyclic Chemistry, Edited by A. R. Katritzky and A. J. Boulton, Academic Press, R. J. Kobylecki and A. Mc Killop, Vol. 19, 215 (1976); W. L. F. Armarego, J. Appl. Chem, 11, 70, (1961).; A. Abdulqader; A. M. Atef; L. Eric J, J. Med. Chem. 28, 1394–8, (1985)).

In accordance with the present invention, compounds of formula I, having the heterocyles 9 to 11, may be prepared to the following Scheme I.

Scheme I

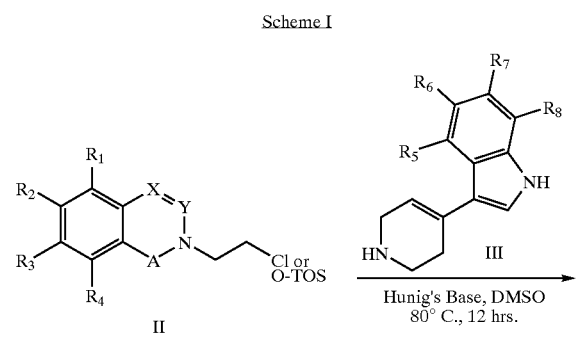

Thus, compound of formula II (where in X=N; Y=CH; A=C=O, heterocycle 9, X=Y=N; A=C=O, heterocycle 10, X=N; Y=CH; A=SO$_2$ heterocycle 11) is reacted with compound of formula III, Hunig's base in DMSO at 80° C. to give a compound of formula I.

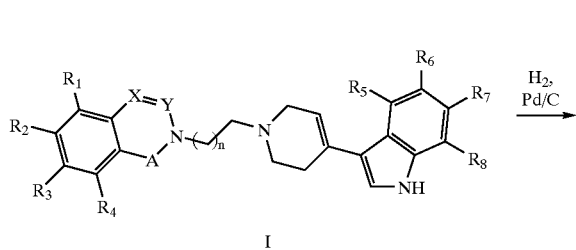

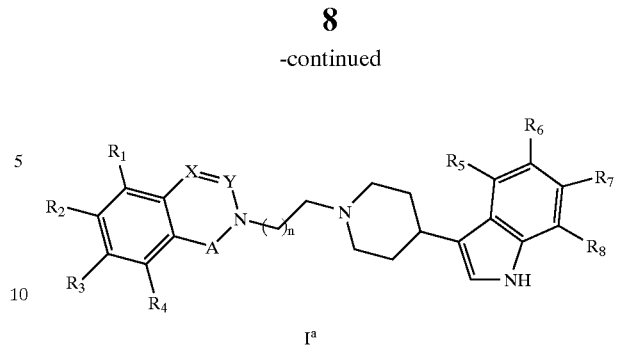

The compound of formula I can be further hydrogenated using catalytic Pd/C and hydrogen pressure in a parr apparatus to give the saturated piperdinyl

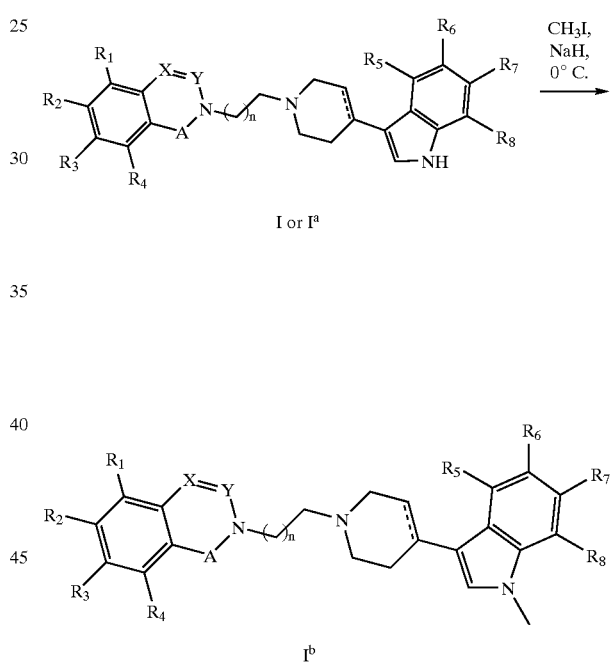

product I$^a$.

Compounds of formula I or I$^a$ can be alkylated at the indole nitrogen using sodium hydride and and an appropriately substituted alkyl iodide at 0° C. to give the substituted product I$^b$.

In accordance with the present invention, compounds of formula II may be prepared to the following Scheme II.

Scheme II

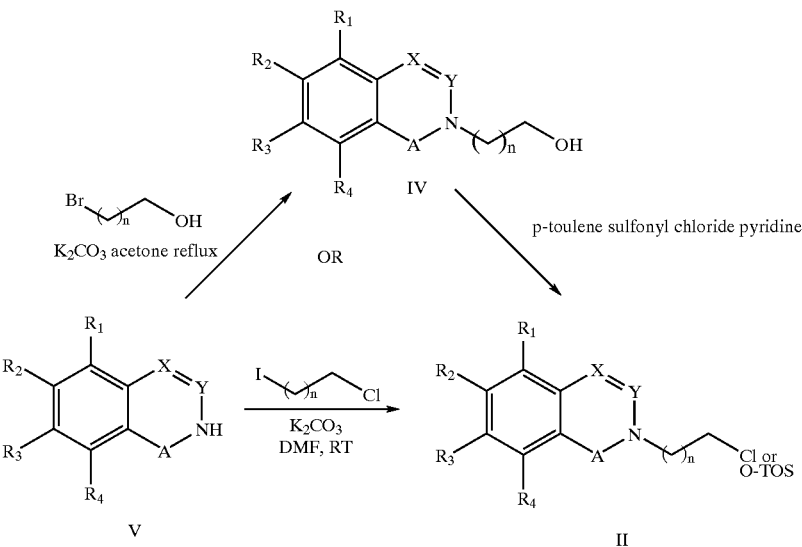

Thus compounds of formula IV are reacted with p-toulene sulfonyl chloride in pyridine to give compounds of formula II. Compounds of formula V are reacted with the appropriate bromo-alcohol using potassium carbonate in acetone at reflux to give compounds of formula IV. Similar reactions may be carried out to synthesize compounds based on 1,2,4-triazolo pyridinone, 8.

The following examples are presented to illustrate certain embodiments of the present invention, but should not be construed as limiting the scope of this invention.

EXAMPLE 1

3-[2-(4-(1H-indol-3-yl)-3,6-dihydro-1(2H)-pyridinyl)ethyl]-6-7-dimethoxy-4(3H)-quinazolinone

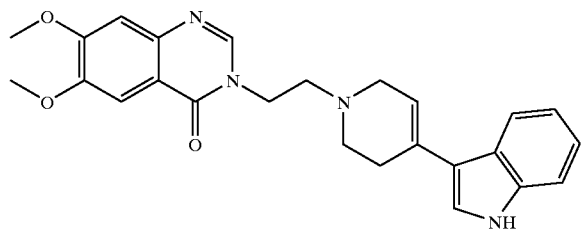

Step 1

3-(2-hydroxyethyl)-6,7-dimethoxy-4(3H)-quinazolinone 3-(2-hydroxyethyl)-6,7-dimethoxy-4(3H)-quinazolinone was prepared from 6,7-dimethoxy-4(3H)-quinazolinone (3 g, 14.6 mmol). The quinazolinone was combined with 2-bromoethanol (1.14 mL, 16 mmol), an excess of potassium carbonate (10 g) and heated at reflux in 200 mL acetone. The salts were filtered off and the reaction mixture was concentrated. The residue was dissolved in chloroform and washed with water. The organic layer was dried over $Na_2SO_4$, filtered and concentrated, 1.39 g (38%); light brown powder; m.p. 130° C., MS: 250.9 (M+H)$^+$ Step 2

2-(6,7-dimethoxy-4-oxo-3(4H)-quinazolinyl)ethyl 4-methyl benzenesulfonate 2-(6,7-dimethoxy-4-oxo-3(4H)-quinazolinyl)ethyl 4-methyl benzenesulfonate was prepared from 3-(2-hydroxyethyl)-6,7-dimethoxy-4(3H)-quinazolinone (1.39 g, 5.56 mmol). The quinazolinone was diluted in pyridine (10 mL) and cooled to 0° C. in an ice water bath. p-Toluene sulfonyl chloride (1.17 g, 6.12 mmol) was added and the mixture stirred at 0° C. then warmed to room temperature overnight. The reaction was quenched with water and the product crashed out and was collected, then washed with water, ether and ethyl acetate and dried, 1.21 g (54%); light brown powder; m.p. 170° C., MS: 404.7 (M+H)$^+$ Step 3

3-[2-(4-(1H-indol-3-yl)-3,6-dihydro-1(2H)-pyridinyl)ethyl]-6-7-dimethoxy-4(3H)-quinazolinone A mixture of 2-(6,7-dimethoxy-4-oxo-3(4H)-quinazolinyl)ethyl 4-methyl benzenesulfonate (0.5 g, 1.24 mmol), 3-(1,2,3,6-tetrahydro-4-pyridinyl)1-H-indole (0.244 g, 1.24 mmol) and diisopropyl ethylamine (3 ml, excess) was heated in DMSO (50 ml) at 100° C. for 24 hrs. At the end reaction mixture was quenched with water and extracted with chloroform. The organic layer was dries over anhydrous $MgSO_4$; filtered and concentrated. The brown gum obtained was purified by $SiO_2$ column chromatography by eluting it with ethyl acetate; hexane (3:1) and 0.16 g of 3-[2-(4-(1H-indol-3-yl)-3,6-dihydro-1(2H)-pyridinyl) ethyl]-6-7-dimethoxy-4(3H)-quinazolinone was isolated as a yellow powder. Yield 30%; mp 219° C.; MS: 430.9 (M+H)$^+$; $^1$H NMR (300 MHz, DMSO-$d_6$): δ 2.51 (m, 2H), 2.73 (d, J=4.02 Hz, 4H), 3.19 (s, 2H), 3.88 (s, 3H), 3.91 (s, 3H) 4.16 (t, J=4.47 Hz, 2H), 6.02 (t, 1H), 6.99 (m, 1H), 7.09 (m, 2H), 7.37 (m, 2H), 7.47 (s, 1H), 7.78 (d, 1H), 8.25 (s, 1H), 11.1 (s, 1H).

EXAMPLE 2

3-{2-[4-(1H-indol-3-yl)-1-piperidinyl]ethyl}-6-7-dimethoxy-4(3H)-quinazolinone

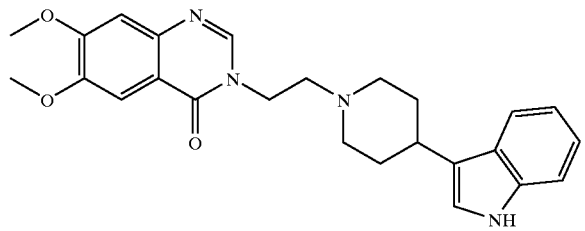

Catalytic 10% Pd/C was added to a dried hydrogenation bottle under $N_2$ and slowly under nitrogen 3-[2-(4-(1H-indol-3-yl)-3,6-dihydro-1(2H)-pyridinyl)ethyl]-6-7-dimethoxy-4(3H)-quinazolinone (0.09 g, 0.2 mmol) in 150 mL of ethanol was added. This sample was hydrogenated at 30–40 psi hydrogen pressure overnight. The mixture was filtered over celite and concentrated then chromatographed; 0.02 g of 3-{2-[4-(1H-indol-3-yl)-1-piperidinyl]ethyl}-6-7-dimethoxy-4(3H)-quinazolinone was isolated as a yellow solid. Yield 23%; mp 230° C.; MS: 432.8 (M+H)$^+$; $^1$H NMR (300 MHz, CDCl$_3$): δ 1.83 (m, 2H), 2.08–2.4 (b, 4H), 2.78 (t, 2H), 2.80 (m, 1H), 3.07 (m, 2H), 4.00 (s, 6H) 4.17 (t, J=4.62 Hz, 2H), 6.97 (d, 1H), 7.12 (m, 2H), 7.17 (t, 1H), 7.36 (d, 1H), 7.97 (s, 1H), 8.06 (s, 1H).

EXAMPLE 3

3-[2-(4-(5-fluoro-1H-indol-3-yl)-3,6-dihydro-1(2H)-pyridinyl)ethyl]-6-7-dimethoxy-4(3H)-quinazolinone

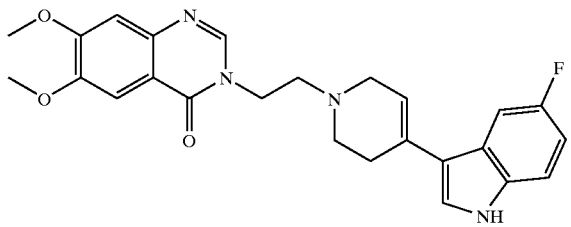

Starting from 2-(6,7-dimethoxy-4-oxo-3(4H)-quinazolinyl)ethyl 4-methylbenzenesulfonate (0.322 g, 0.80 mmol) and 5-fluoro-3-[4-(1,2,3,6-tetrahydropyridinyl)]indole (0.207 g, 0.956 mmol), following the same procedure as in example 1, step 3, 0.265 g of 3-[2-(4-(5-fluoro-1H-indol-3-yl)-3,6-dihydro-1(2H)-pyridinyl)ethyl]-6-7-dimethoxy-4(3H)-quinazolinone was isolated as an orange solid. Yield 74%; mp 210° C.; MS: 448.8 (M+H)$^+$; $^1$H NMR (300 MHz, CDCl$_3$): δ 2.58 (t, 2H), 2.83 (t, J=4.32 Hz, 2H), 2.88 (t, J=4.68 Hz, 2H), 3.31 (m, 2H), 3.99 (s, 3H), 4.00 (s, 3H), 4.20 (t, J=4.71 Hz, 2H), 6.09 (t, 1H), 6.95 (m, 1H), 7.09 (s, 1H), 7.19 (d, 1H), 7.28 (m, 1H), 7.55 (d of d, 1H), 7.64 (s, 1H), 8.04 (s, 1H).

EXAMPLE 4

3-[4-(4-(1H-indol-3-yl)-3,6-dihydro-1(2H)-pyridinyl)butyl]-6-7-dimethoxy-4(3H)-quinazolinone

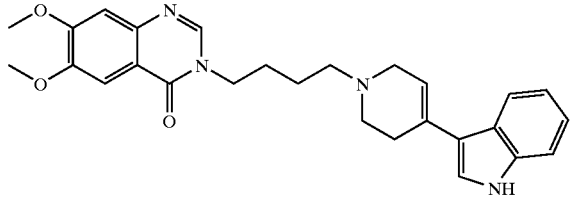

Step 1

3-(4-chlorobutyl)-6,7-dimethoxy-4(3H)-quinazolinone 3-(4-chlorobutyl)-6,7-dimethoxy-4(3H)-quinazolinone was prepared starting from 6,7-dimethoxy-4(3H)-quinazolinone (1.65 g, 8 mmol). The quinazolinone was combined with 1-chloro-4-iodobutane (1.08 mL, 8.8 mmol), an excess of potassium carbonate (10 g) and stirred in 30 mL DMF overnight. The salts were filtered off and the reaction mixture was dilluted with water. The solid that formed was collected via vacuum filtration, washed with water and dried, 1.55 g (65%); gray solid; m.p. 117° C., MS: 296.8 (M+H)$^+$

Step 2

3-[4-(4-(1H-indol-3-yl)-3,6-dihydro-1(2H)-pyridinyl)butyl]-6-7-dimethoxy-4(3H)-quinazolinone Starting from 3-(4-chlorobutyl)-6,7-dimethoxy-4(3H)-quinazolinone (0.5 g, 1.69 mmol) and 3-(1,2,3,6-tetrahydro-4-pyridinyl)1-H-indole (0.330 g, 1.69 mmol), following the same procedure as in example 1, step 3; 0.23 g of 3-[4-(4-(1H-indol-3-yl)-3,6-dihydro-1(2H)-pyridinyl)butyl]-6-7-dimethoxy-4(3H)-quinazolinone was isolated as a yellow powder. Yield 30%; mp 136° C.; MS: 458.8 (M+H)$^+$; $^1$H NMR (300 MHz, DMSO-d$_6$): δ 1.52 (m, 2H), 1.74 (m, 2H), 2.50 (d, J=1.35 Hz, 4H), 2.62 (m, 2H), 3.10 (m, 2H), 3.87 (s, 3H), 3.90 (s, 3H) 4.01 (t, J=5.34 Hz, 2H), 6.10 (t, 1H), 7.02 (m, 1H), 7.08 (m, 1H), 7.14 (s, 1H), 7.37 (m, 2H), 7.48 (s, 1H), 7.78 (d, 1H), 8.31 (s, 1H), 11.1 (s, 1H).

EXAMPLE 5

3-{4-[4-(1H-indol-3-yl)-1-piperdinyl]butyl}-6,7-dimethoxy-4(3H)-quinazolinone

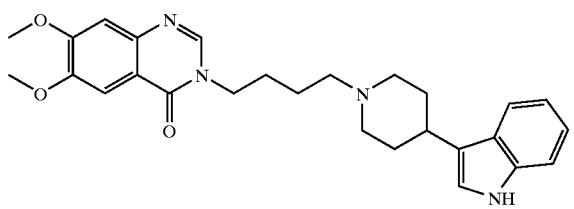

Starting from 3-[4-(4-(1H-indol-3-yl)-3,6-dihydro-1(2H)-pyridinyl)butyl]-6-7-dimethoxy-4(3H)-quinazolinone (0.16 g, 0.35 mmol), following the same procedure as in example 2, 0.023 g of 3-{4-[4-(1H-indol-3-yl)-1-piperdinyl]butyl}-6-7-dimethoxy-4(3H)-quinazolinone was isolated as an off white powder. Yield 14%; mp 148° C.; MS: 460.9 (M+H)+; 1H NMR (300 MHz, CDCl3): δ 1.72 (m, 2H), 1.84 (m, 4H), 2.06 (m, 4H), 2.22 (m, 1H), 2.56 (m, 2H), 3.13 (m, 2H), 4.00 (s, 6H) 4.04 (t, J=5.37 Hz, 2H), 6.99 (t, 1H), 7.12 (m, 2H), 7.16 (t, 1H), 7.30 (d, 1H), 7.63 (d, 2H), 7.96 (s, 1H).

EXAMPLE 6

3-[3-(4-(1H-indol-3-yl)-3,6-dihydro-1(2H)-pyridinyl)propyl]-6-7-dimethoxy-4(3H)-quinazolinone

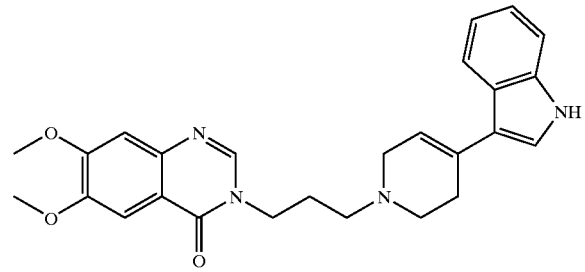

Step 1

3-(3-chloropropyl)-6,7-dimethoxy-4(3H)-quinazolinone 3-(3-chloropropyl)-6,7-dimethoxy-4(3H)-quinazolinone was prepared starting from 6,7-dimethoxy-4-(3H) quinazolinone (1.61 g, 8 mmol). The quinazolinone was combined with 1-chloro-3-iodopropane (1.9 mL, 8 mmol), an excess of potassium carbonate (10 g) and stirred in 30 mL DMF overnight. The salts were filtered off and the reaction mixture dilluted with water. The solid that formed was collected via vacuum filtration, washed with water and dried, 0.70 g (31%); brown solid; m.p. 143° C., MS: 282.8 (M+H)+

Step 2

3-[3-(4-(1H-indol-3-yl)-3,6-dihydro-1(2H)-pyridinyl)propyl]-6-7-dimethoxy-4(3H)-quinazolinone Starting from 3-(3-chloropropyl)-6,7-dimethoxy-4(3H)-quinazolinone (0.5 g, 1.77 mmol) and 3-(1,2,3,6-tetrahydro-4-pyridinyl)1-H-indole (0.349 g, 1.77 mmol), following the same procedure as in example 1, step 3, 0.30 g of 3-[3-(4-(1H-indol-3-yl)-3,6-dihydro-1(2H)-pyridinyl)propyl]-6-7-dimethoxy-4(3H)-quinazolinone was isolated as an orange solid. Yield 38%; mp 120° C.; MS: 444.9 (M+H)+; 1H NMR (300 MHz, CDCl3): δ 2.08 (t, 2H), 2.53 (t, J=4.98 Hz, 2H), 2.62 (m, 2H), 2.73 (t, J=4.38 Hz, 2H), 3.21 (m, 2H), 3.95 (s, 3H), 4.00 (s, 3H), 4.15 (t, 2H), 6.20 (t, 1H), 7.09 (s, 1H), 7.17 (m, 3H), 7.37 (d, 1H), 7.64 (s, 1H), 7.89 (d, 1H), 8.10 (s, 1H).

EXAMPLE 7

3-{3-(4-(1H-indol-3-yl)-1-piperidinyl]propyl}-6-7-dimethoxy-4(3H)-quinazolinone

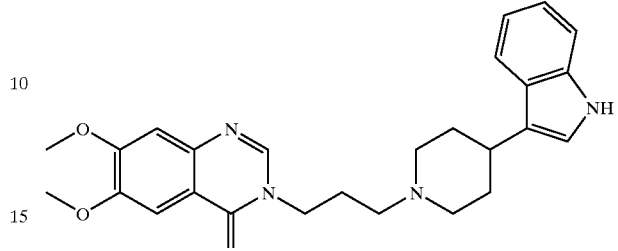

Starting from 3-[3-(4-(1H-indol-3-yl)-3,6-dihydro-1(2H)-pyridinyl)propyl]-6-7-dimethoxy-4(3H)-quinazolinone (0.25 g, 0.5 mmol), following the same procedure as in example 2, 0.02 g of 3-{3-[4-(1H-indol-3-yl)-1-pyridinyl]propyl}-6-7-dimethoxy-4(3H)-quinazolinone was isolated as a yellow powder. Yield 9%; mp 168° C.; MS: 447.0 (M+H)+; 1H NMR (300 MHz, CDCl3): δ 1.86 (m, 2H), 2.05 (m, 4H), 2.21 (m, 2H), 2.53 (m, 2H), 2.87 (m, 1H), 3.11 (m, 2H), 4.0 (d, 6H), 4.12 (t, J=5.01 Hz, 2H), 6.97 (d, 1H), 7.11 (m, 2H), 7.17 (t, 1H), 7.37 (d, 1H), 7.63 (t, 3H), 8.01 (s, 1H), 8.10 (s, 1H).

EXAMPLE 8

3-[3-(4-(5-fluoro-1H-indol-3-yl)-3,6-dihydro-1(2H)-pyridinyl)propyl]-6-7-dimethoxy-4(3H)-quinazolinone

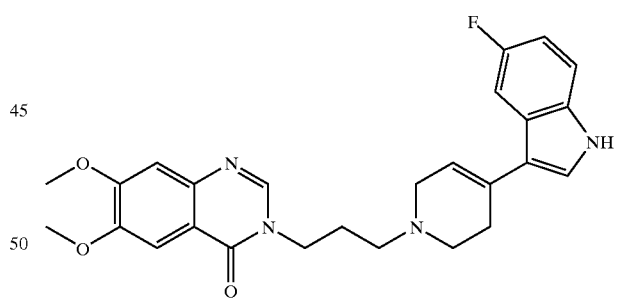

Starting from 3-(3-chloropropyl)-6,7-dimethoxy-4(3H)-quinazolinone (0.120 g, 0.4 mmol) and 5-fluoro-3-[4-(1,2,3,6-tetrahydropyridinyl)]indole (0.120 g, 0.55 mmol), following the same procedure as in example 1, step 3, 0.01 g of 3-[3-(4-(5-fluoro-1H-indol-3-yl)-3,6-dihydro-1(2H)-pyridinyl)propyl]-6-7-dimethoxy-4(3H)-quinazolinone was isolated as an orange solid. Yield 5%; mp 120° C.; MS: 463.2 (M+H)+; 1H NMR (300 MHz, CDCl3): δ 1.26 (m, 2H), 2.12 (t, 2H), 2.60 (m, 2H), 2.78 (m, 2H), 3.49 (m, 2H), 3.97 (s, 3H), 4.00 (s, 3H), 4.15 (t, 2H), 6.10 (t, 1H), 6.96 (m, 1H), 7.09 (s, 1H), 7.20 (s, 1H), 7.28 (m, 1H), 7.51 (d, 1H), 7.63 (s, 1H), 8.09 (s, 1H).

EXAMPLE 9

8-bromo-6-chloro-3-[3-(4-(1H-indol-3-yl)-3,6-dihydro-1(2H)-pyridinyl)propyl]-4(3H)-quinazolinone

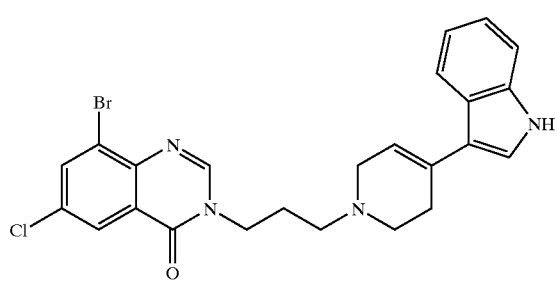

Step 1

8-Bromo-6-chloro-4(3H) quinazolinone

8-Bromo-6-chloro-4(3H) quinazolinone was prepared from 2-amino-3-bromo-5-chlorobenzoic acid (10 g, 40 mmol). The acid was heated in excess formamide (50 mL) at reflux overnight. The mixture was cooled and quenched with water. The solid that formed was washed with acetonitrile, 6.7 g crude (65%); MS: 260.8 (M+H)$^+$

Step 2

3-(4-chloropropyl)-(8-bromo-6-chloro)-4(3H)-quinazolinone 3-(4-chloropropyl)-(8-bromo-6-chloro)-4(3H)-quinazolinone was prepared according to the procedure outlined in example 6, step 1. Starting from 8-bromo-6-chloro-4(3H)-quinazolinone (5 g, 19.3 mmol) and 1-chloro-3-iodopropane (2.07 mL, 21.2 mmol), 3.45 g (53%); white powder, MS: 336.9 (M+H)$^+$

Step 3

8-bromo-6-chloro-3-[3-(4-(1H-indol-3-yl)-3,6-dihydro-1(2H)-pyridinyl)propyl]-4(3H)-quinazolinone Starting from 3-(4-chloropropyl)-(8-bromo-6-chloro)-4(3H)-quinazolinone (2 g, 5.97 mmol) and 3-(1,2,3,6-tetrahydro-4-pyridinyl)1-H-indole (1.18 g, 5.97 mmol), following the same procedure as in example 1, step 3; 2.13 g of 8-bromo-6-chloro-3-[3-(4-(1H-indol-3-yl)-3,6-dihydro-1(2H)-pyridinyl)propyl]-4(3H)-quinazolinone was isolated as a yellow powder. Yield 72%; mp 192° C.; MS: 499.3 (M+H)$^+$; $^1$H NMR (300 MHz, DMSO-d$_6$): δ 1.95 (t, J=5.07 Hz, 2H), 2.47 (m, 4H), 2.60 (m, 2H), 3.09 (m, 2H), 4.08 (t, J=5.22 Hz, 2H), 6.06 (t, 1H), 6.99 (t, J=5.22 Hz, 1H), 7.09 (t, J=5.25 Hz, 1H), 7.34 (m, 1H), 7.75 (d, 1H), 8.10 (d, J=1.77 Hz, 1H), 8.18 (d, J=1.8 Hz, 1H), 8.54 (s, 1H), 11.1 (s, 1H).

EXAMPLE 10

6-chloro-3-[3-(4-(1H-indol-3-yl)-3,6-dihydro-1(2H)-pyridinyl)propyl]-4(3H)-quinazolinone

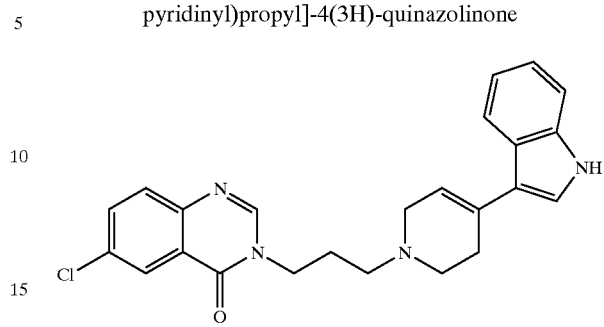

Catalytic 10% Pd/C was added to a dried hydrogenation bottle under N$_2$ and slowly under nitrogen 8-bromo-6-chloro-3-[3-(4-(1H-indol-3-yl)-3,6-dihydro-1(2H)-pyridinyl)propyl]-4(3H)-quinazolinone (1.52 g, 3.05 mmol) in 150 mL of ethanol was added. This sample was hydrogenated at 30–40 psi hydrogen pressure overnight. The mixture was filtered over celite and concentrated then chromatographed; 6-chloro-3-[3-(4-(1H-indol-3-yl)-3,6-dihydro-1(2H)-pyridinyl)propyl]-4(3H)-quinazolinone was isolated as a yellow powder (0.47 g). Yield 37%; mp 170° C.; MS: 418.8 (M+H)$^+$; $^1$H NMR (300 MHz, DMSO-d$_6$): δ 2.14 (m, 2H), 2.51 (m, 4H), 2.67 (m, 2H), 3.31 (m, 2H), 4.10 (t, J=4.8 Hz), 6.15 (t, 1H), 7.06 (m, 2H), 7.36 (d, 1H), 7.75 (m, 1H), 7.80 (m, 2H), 8.12 (d, 1H), 8.32 (s, 1H), 8.45 (s, 1H), 11.2 (s, 1H).

EXAMPLE 11

6-chloro-3-{3-[4-(1H-indol-3-yl)-1-piperidinyl]propyl}-4(3H)-quinazolinone

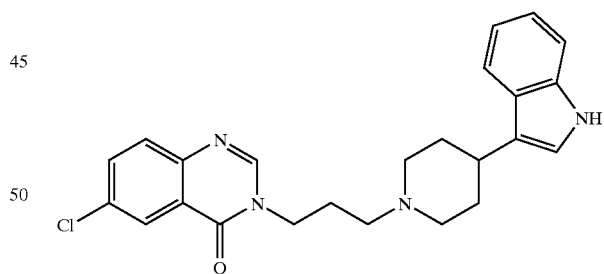

Starting from 6-chloro-3-[3-(4-(1H-indol-3-yl)-3,6-dihydro-1(2H)-pyridinyl)propyl]-4(3H)-quinazolinone (0.37 g, 0.9 mmol), following the same procedure as in example 2, 0.02 g of 6-chloro-3-{3-[4-(1H-indol-3-yl)-1-piperidinyl]propyl}-4(3H)-quinazolinone was isolated as a yellow powder. Yield 5%; mp 138° C.; MS: 420.9 (M+H)$^+$; $^1$H NMR (300 MHz, CDCl$_3$): δ 1.90 (m, 2H, 2.07 (m, 4H), 2.27 (m, 2H), 2.58 (m, 2H), 2.88 (m, 1H), 3.15 (d, 2H), 4.14 (t, J=5.01 Hz, 2H), 6.98 (d, 1H), 7.09 (t, 1H), 7.19 (t, J=5.28 Hz, 1H), 7.36 (d, 1H), 7.64 (m, 3H), 8.05 (s, 1H), 8.19 (s, 1H), 8.28 (d, 1H).

EXAMPLE 12

3-[2-(4-(1H-indol-3-yl)-3,6-dihydro-1(2H)-pyridinyl)ethyl]-4(3H)-quinazolinone

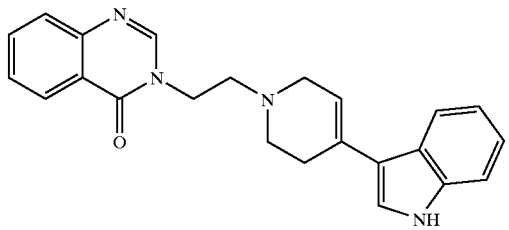

Starting from 3-(4-chloroethyl)-4(3H)-quinazolinone (2.20 g, 10.6 mmol) and 3-(1,2,3,6-tetrahydro-4-pyridinyl)-1-H-indole (2.08 g, 10.6 mmol), following the same procedure as in example 1, step 3, 2.41 g of 3-[2-(4-(1H-indol-3-yl)-3,6-dihydro-1(2H)-pyridinyl)ethyl]-4(3H)-quinazolinone was isolated as a yellow powder. Yield 61%; mp 132° C.; MS: 371.3 (M+H)+; $^1$H NMR (300 MHz, DMSO-$d_6$): δ 2.49 (m, 2H), 2.75 (m, 4H), 3.20 (m, 2H), 4.18 (t, J=4.5 Hz, 2H), 6.09 (t, 1H), 7.00 (t, J=4.8 Hz, 1H), 7.09 (t, J=5.4 Hz, 1H), 7.37 (m, 2H), 7.54 (t, 1H), 7.65 (d, 1H), 7.81 (m, 2H), 8.17 (d, 1H), 8.35 (s, 1H), 11.1 (s, 1H).

EXAMPLE 13

3-{2-[4-(1H-indol-3-yl)-1-piperidinyl]ethyl}-4(3H)-quinazolinone

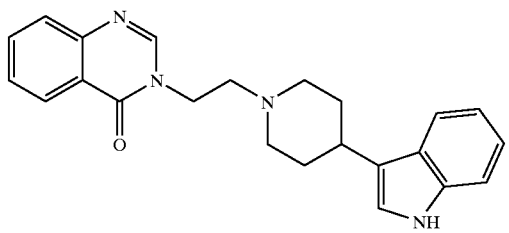

Starting from 3-[2-(4-(1H-indol-3-yl)-3,6-dihydro-1(2H)-pyridinyl)ethyl]-4(3H)-quinazolinone (1.33 g, 3.59 mmol), following the same procedure as in example 2, 0.43 g of 3-{2-[4-(1H-indol-3-yl)-1-piperidinyl]ethyl}-4(3H)-quinazolinone was isolated as a brown solid. Yield 11%; mp 90° C.; MS: 372.9 (M+H)+; $^1$H NMR (300 MHz, CDCl$_3$): δ 1.78 (m, 2H), 2.05 (m, 2H), 2.33 (m, 2H), 2.78 (m, 2H), 2.87 (m, 1H), 3.03 (m, 2H), 4.17 (t, J=4.41 Hz, 2H), 6.96 (d, 1H), 7.09 (m, 1H), 7.18 (t, J=5.94 Hz, 1H), 7.37 (d, 1H), 7.51 (m, 1H), 7.62 (d, 1H), 7.77 (m, 2H), 8.01 (s, 1H), 8.14 (s, 1H), 8.32 (d, 1H).

EXAMPLE 14

3-{2-[4-(1-methyl-1H-indol-3-yl)-1-piperidinyl]ethyl}-4-(3H)-quinazolinone

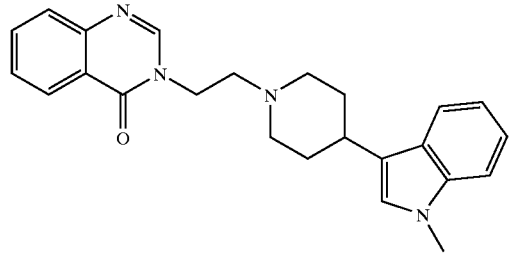

Step 1

3-[2-(4-(1-methyl-1H-indol-3-yl)-3,6-dihydro-1(2H)-pyridinyl)ethyl]-4(3H)-quinazolinone A dried flask under nitrogen was loaded with sodium hydride (0.015 g, 0.37 mmol) and THF (10 mL). At 0° C. 3-[2-(4-(1H-indol-3-yl)-3,6-dihydro-1(2H)-pyridinyl)ethyl]-4(3H)-quinazolinone (0.80 g, 2.16 mmol), was added and the mixture stirred for 15 minutes. Keeping the reaction temperature at 0° C., the iodomethane was added dropwise (0.14 mL, 2.16 mmol). This was allowed to warm to room temperature and stir overnight. Water was slowly added to the mixture to quench and the organics were extracted in chloroform, washed with water and dried over Na$_2$SO$_4$, filtered and concentrated. The residue was chromatograhed using silica (2% methanol:chloroform system); 0.52 g of 3-[2-(4-(1-methyl-1H-indol-3-yl)-3,6-dihydro-1(2H)-pyridinyl)ethyl]-4(3H)-quinazolinone was isolated as an orange solid. Yield 63%; MS: 384.9 (M+H)+; $^1$H NMR (300 MHz, CDCl$_3$): δ 2.79 (m, 2H), 3.17 (m, 4H), 3.20 (m, 2H), 3.61 (m, 2H), 3.76 (s, 3H), 4.44 (t, 2H), 6.12 (t, 1H), 7.00 (t, 1H), 7.37 (m, 1H), 7.53 (m, 1H), 7.45 (m, 2H), 7.81 (m, 1H), 8.17 (d, 1H), 8.35 (s, 1H).

Step 2

3-{2-[4-(1-methyl-1H-indol-3-yl)-1-piperidinyl]ethyl}-4-(3H)-quinazolinone

Starting from 3-[2-(4-(1-methyl-1H-indol-3-yl)-3,6-dihydro-1(2H)-pyridinyl)ethyl]-4(3H)-quinazolinone (0.430 g, 1.12 mmol), following the same procedure as in example 2, 0.044 g of 3-{2-[4-(1-methyl-1H-indol-3-yl)-1-piperidinyl]ethyl}-4-(3H)-quinazolinone was isolated as an orange solid. Yield 10%; mp 78° C.; MS: 386.9 (M+H)+; $^1$H NMR (300 MHz, CDCl$_3$): δ 1.62 (m, 4H), 2.08 (m, 2H), 2.53 (m, 1H), 2.92 (m, 2H), 3.22 (m, 2H), 3.75 (s, 3H), 4.29 (m, 2H), 6.79 (s, 1H), 7.11 (m, 1H), 7.21 (m, 1H), 7.27 (m, 2H), 7.50 (m, 1H), 7.59 (d, 1H), 7.76 (m, 2H), 8.32 (d, 1H).

EXAMPLE 15

6-fluoro-3-{2-[4-(1H-indol-3-yl)-3,6-dihydro-1(2H)-pyridinyl]ethyl}-4(3H)-quinazolinone

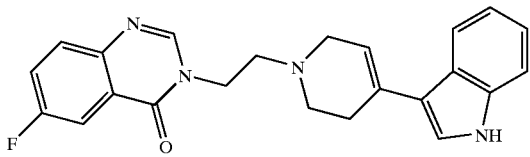

Starting from 3-(4-chloroethyl)-6-fluoro-4(3H)-quinazolinone (0.56 g, 2.5 mmol) and 3-(1,2,3,6-tetrahydro-4-pyridinyl)1-H-indole (0.49 g, 2.5 mmol), following the same procedure as in example 1, step 3; 0.035 g of 6-fluoro-3-{2-[4-(1H-indol-3-yl)-3,6-dihydro-1(2H)-pyridinyl]ethyl}-4(3H)-quinazolinone was isolated as a tan powder. Yield 4%; mp 138° C.; MS: 388.9 (M+H)$^+$; $^1$H NMR (300 MHz, DMSO-d$_6$): δ 2.49 (m, 2H), 2.74 (m, 4H), 3.19 (m, 2H), 4.18 (t, J=4.53 Hz, 2H), 6.09 (t, 1H), 7.00 (t, J=5.4 Hz, 1H), 7.09 (t, J=5.4 Hz, 1H), 7.37 (m, 2H), 7.70–7.86 (band, 4H), 8.36 (s, 1H), 11.1 (s, 1H).

EXAMPLE 16

3-[2-(4-(1H-indol-3-yl)-3,6-dihydro-1(2H)-pyridinyl)ethyl]-1,2,3-benzotriazin-4(3H)-one

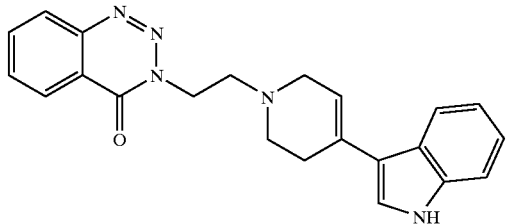

Step 1

3-(2-hydroxyethyl)-1,2,3-benzotriazin-4(3H)one 3-(2-hydroxyethyl)-1,2,3-benzotriazin-4(3H)one was prepared according to the general procedure outlined in example 1, step 1. Starting from 1,2,3-benzotriazin-4(3H)one (1.5 g, 10 mmol) and 2-bromoethanol (1.68 mL, 20 mmol), 1.20 g (63%); off white solid; m.p. 114° C., MS: 191.9 (M+H)$^+$

Step 2

2-(4-oxo-1,2,3-benzotriazin-3(4H)-yl)ethyl-4-methyl benzenesulfonate 2-(4-oxo-1,2,3-benzotriazin-3(4H)-yl)ethyl-4-methyl benzenesulfonate was prepared according to the general procedure outlined in example 1, step 2. Starting from 3-(2-hydroxyethyl)-1,2,3-benzotriazin-4(3H)one (0.5 g, 2.6 mmol) and p-toulene sulfonyl chloride (0.55 g, 2.9 mmol), 0.81 g (90%); white crystals; m.p. 161° C., MS: 345.7 (M+H)$^+$

Step 3

3-[2-(4-(1H-indol-3-yl)-3,6-dihydro-1(2H)-pyridinyl)ethyl]-1,2,3-benzotriazin-4(3H)-one Starting from 2-(4-oxo-1,2,3-benzotriazin-3(4H)-yl)ethyl-4-methyl benzenesulfonate (0.68 g, 1.97 mmol) and 3-(1,2,3,6-tetrahydro-4-pyridinyl)1-H-indole (0.39 g, 1.97 mmol), following the same procedure as in example 1, step 3; 0.45 g of 3-[2-(4-(1H-indol-3-yl)-3,6-dihydro-1(2H)-pyridinyl)ethyl]-1,2,3-benzotriazin-4(3H)-one was isolated as a yellow powder. Yield 62%; mp 230° C.; MS: 371.9 (M+H)$^+$; $^1$H NMR (300 MHz, DMSO-d$_6$): δ 2.46 (s, 2H), 2.75 (m, 2H), 2.92 (m, 2H), 3.23 (m, 2H), 4.61 (t, J=4.86 Hz, 2H), 6.09 (t, 1H), 6.98 (t, J=5.1 Hz, 1H), 7.09 (t, J=5.1 Hz, 1H), 7.36 (m, 2H), 7.77 (t, 1H), 7.93 (t, 1H), 8.08 (t, 1H), 8.20 (d, 1H), 8.28 (d, 1H), 11.1 (s, 1H).

EXAMPLE 17

3-{2-[4-(1H-indol-3-yl)-1-piperidinyl)ethyl}-1,2,3-benzotriazin-4(3H)-one

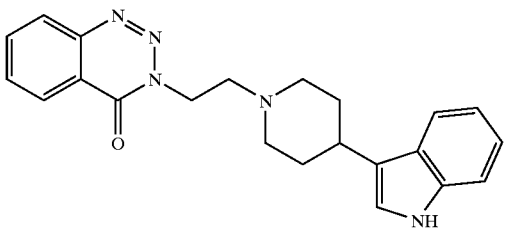

Starting from 3-[2-(4-(1H-indol-3-yl)-3,6-dihydro-1(2H)-pyridinyl)ethyl]-1,2,3-benzotriazin-4(3H)-one (0.32 g, 0.86 mmol), following the same procedure as in example 2, 0.17 g of 3-{2-[4-(1H-indol-3-yl)-1-piperidinyl]ethyl}-1,2,3-benzotriazin-4(3H)-one was isolated as a white powder. Yield 53%; mp 171° C.; MS: 373.9 (M+H)$^+$; $^1$H NMR (300 MHz, CDCl$_3$): δ 1.80 (q, 2H), 2.07 (d, 2H), 2.31 (t, 2H), 2.84 (m, 1H), 2.96 (t, 2H), 3.17 (d, 2H), 4.67 (t, J=5.16 Hz, 2H), 6.95 (d, 1H), 7.11 (t, 1H), 7.18 (t, 1H), 7.34 (d, 1H), 7.62 (d, 1H), 7.80 (m, 1H), 7.95 (m, 2H), 8.15 (d, 1H), 8.38 (d, 1H).

EXAMPLE 18

3-{2-[4-(1-methyl-1H-indol-3-yl)-1-piperidinyl]ethyl}-1,2,3-benzotriazin-4(3H)-one

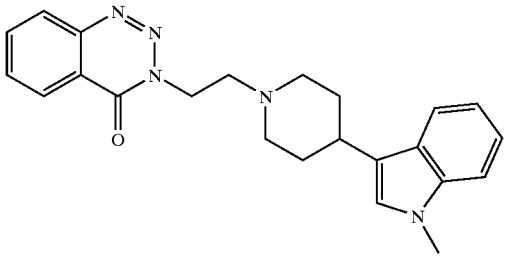

A dried flask under nitrogen was loaded with sodium hydride (0.015 g, 0.37 mmol) and THF (10 mL). At 0° C. 3-{2-[4-(1H-indol-3-yl)-1-piperidinyl]ethyl}-1,2,3-benzotriazin-4(3H)-one (0.07 g, 0.19 mmol), was added and the mixture stirred for 15 minutes. Keeping the reaction temperature at 0° C., the iodomethane was added dropwise (0.01 mL, 0.19 mmol). This was allowed to warm to room temperature and stir overnight. Water was slowly added to the mixture to quench and the organics were extracted in chloroform, washed with water and dried over Na$_2$SO$_4$, filtered and concentrated. The residue was chromatograhed using silica and a 2% methanol:chloroform system. 0.03 g of 3-{2-[4-(1-methyl-1H-indol-3-yl)-1-piperidinyl]ethyl}-1,2,3-benzotriazin-4(3H)-one was isolated as an orange solid.

Yield 41%; MS: 388.3 (M+H)⁺; ¹H NMR (300 MHz, CDCl₃): δ 1.80 (q, 2H), 2.03 (d, 2H), 2.31 (t, 2H), 2.81 (m, 1H), 2.96 (t, 2H), 3.16 (d, 2H), 3.73 (s, 3H), 4.68 (t, J=5.19 Hz, 2H), 6.79 (s, 1H), 7.06 (t, 1H), 7.20 (t, 1H), 7.28 (m, 1H), 7.60 (d, 1H), 7.81 (t, 1H), 7.95 (t, 1H), 8.16 (d, 1H), 8.37 (d, 1H).

EXAMPLE 19

3-[3-(4-(1H-indol-3-yl)-3,6-dihydro-1(2H)-pyridinyl)propyl]-1,2,3-benzotriazin-4(3H)-one

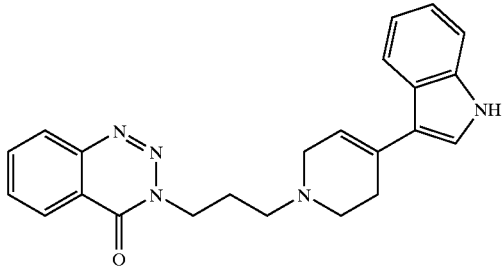

Step 1

3-(3-chloropropyl)-1,2,3-benzotriazin-4(3H)one 3-(3-chloropropyl)-1,2,3-benzotriazin-4(3H)one was prepared according to the general procedure outlined in example 6, step 1. Starting from 1,2,3-benzotriazin-4(3H)one (2 g, 13.6 mmol) and 1-chloro-3-iodopropane (1.6 mL, 14.95 mmol), 1.57 g (52%); yellow solid; m.p. 69° C., MS: 223.9 (M+H)⁺

Step 2

3-[3-(4-(1H-indol-3-yl)-3,6-dihydro-1(2H)-pyridinyl)propyl]-1,2,3-benzotriazin-4(3H)-one Starting from 3-(3-chloropropyl)-1,2,3-benzotriazin-4 (3H)one (1.49 g, 6.68 mmol) and 3-(1,2,3,6-tetrahydro-4-pyridinyl)1-H-indole (1.32 g, 6.68 mmol), following the same procedure as in example 1, step 3; 2.03 g of 3-[3-(4-(1H-indol-3-yl)-3,6-dihydro-1(2H)-pyridinyl)propyl]-1,2,3-benzotriazin-4(3H)-one was isolated as an off white solid. Yield 79%; mp 189° C.; MS: 386.2 (M+H)⁺; ¹H NMR (300 MHz, CDCl₃): δ 2.20 (m, 2H), 2.57 (m, 2H), 2.66 (t, 2H), 2.72 (t, 2H), 3.21 (m, 2H), 4.61 (t, J=5.34 Hz, 2H), 6.15 (t, 1H), 7.12–7.21 (band, 2H), 7.26 (s, 1H), 7.35 (d, 1H), 7.75 (t, 1H), 7.87 (m, 2H), 8.13 (d, 1H), 8.36 (d, 1H).

EXAMPLE 20

3-{3-[4-(1H-indol-3-yl)-1-piperidinyl]propyl}-1,2,3-benzotriazin-4(3H)-one

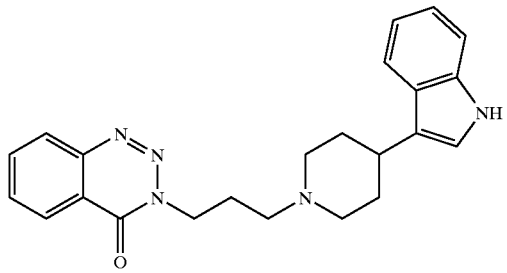

Starting from 3-[3-(4-(1H-indol-3-yl)-3,6-dihydro-1(2H)-pyridinyl)propyl]-1,2,3-benzotriazin-4(3H)-one (1.0 g, 2.6 mmol), following the same procedure as in example 2, 0.18 g of 3-{3-[4-(1H-indol-3-yl)-1-piperidinyl]propyl}-1,2,3-benzotriazin-4(3H)-one was isolated as an orange solid. Yield 18%; mp 60° C.; MS: 388.3 (M+H)⁺; ¹H NMR (300 MHz, CDCl₃): δ 1.66 (m, 2H), 1.98–2.21 (band, 6H), 2.57 (t, 2H), 2.80 (m, 1H), 3.05 (d, 2H), 4.58 (t, J=5.31 Hz, 2H), 6.89 (d, 1H), 7.09 (t, 1H), 7.15 (t, 1H), 7.34 (d, 1H), 7.59 (d, 1H), 7.80 (m, 1H), 7.95 (m, 2H), 8.15 (d, 1H), 8.38 (d, 1H).

EXAMPLE 21

3-[3-(4-(1-methyl-1H-indol-3-yl)-3,6-dihydro-1(2H)-pyridinyl)propyl]-1,2,3-benzotriazin-4(3H)-one

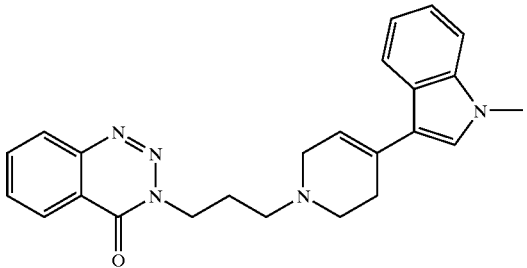

Starting from 3-[3-(4-(1H-indol-3-yl)-3,6-dihydro-1(2H)-pyridinyl)propyl]-1,2,3-benzotriazin-4(3H)-one (0.83 g, 2.2 mmol) and iodomethane (0.14 mL, 2.2 mmol), and following the same procedure as in example 21, 0.31 g of 3-[3-(4-(1-methyl-1H-indol-3-yl)-3,6-dihydro-1(2H)-pyridinyl) propyl]-1,2,3-benzotriazin-4(3H)-one was isolated as an orange solid. Yield 35%; mp 70° C.; MS: 400.3 (M+H)⁺; ¹H NMR (300 MHz, CDCl₃): δ 2.20 (m, 2H), 2.54 (m, 2H), 2.66 (t, 2H), 2.72 (t, 2H), 3.21 (m, 2H), 3.75 (s, 3H), 4.60 (t, J=5.34 Hz, 2H), 6.11 (m, 1H), 6.99 (s, 1H), 7.15 (t, 1H), 7.22 (t, 1H), 7.27 (m, 2H), 7.75 (t, 1H), 7.87 (m, 1H), 8.12 (d, 1H), 8.36 (d, 1H).

EXAMPLE 22

2-{3-[4-(1H-Indol-3-yl)-3,6-dihydro-2H-pyridin-1-yl]-propyl}-2H-[1,2,4]triazolo[4,3-a]pyridin-3-one

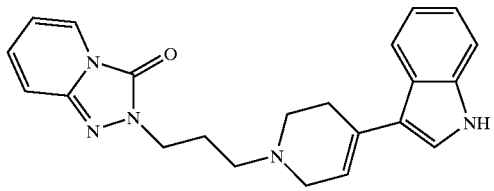

2-(3-Chloro-propyl)-2H-[1,2,4]triazolo[4,3-a]pyridin-3-one was synthesized starting from 1,2,4-triazolo pyridinone. 1,2,4-triazolo pyridinone, 1.35 g(10 mmol) was dissolved in 100 ml DMF. The solution under nitrogen was then added 440 mg NaH(60%, 1.1 eq). The mixture was stirred under nitrogen for half an hour. 3-chloropropanol tosylate was then added all at once and the reaction media was heated at 50° C. for 4 hours. It was then cooled down to room temperature and poured into about 300 ml water and extracted with ethyl acetate (2×200 ml). The combined organic layers were dried over magnesium sulfate and filtered and concentrated. Flash column chromatography using 1:1 mixture of hexane and ethyl acetate yielded 1.216 gram product (58%).

2-(3-Chloro-propyl)-2H-[1,2,4]triazolo[4,3-a]pyridin-3-one 211 mg (1 mmol) was loaded into a round bottomed flask, followed by 396 mg (2 eq) of 3-(1,2,3,6-Tetrahydro-pyridin-4-yl)-1H-indole, 1.0 gram of potassium iodide, 1.0 gram of potassium carbonate, 100 ml acetone. The mixture was stirred under nitrogen for 18 hours. It was then poured into about 300 ml water and extracted with ethyl acetate (2×200 ml). The combined organic layers were dried over magnesium sulfate and filtered and concentrated. Flash column chromatography using 10% ~100% ethyl acetate/hexane and yielded 220 mg of product (59%). mp: 173.3° C. M+: 374.0; (300 MHz, CDCl$_3$): 8.60 (s, 1H, NH), 7.90 (d, 1H), 7.75(d, 1H), 7.34(d, 1H), 7.11(m, 5H), 6.44(m, 1H), 6.16(s, 1H), 4.12 (t, CH2), 3.22 (d, CH2), 2.70 (t, CH2) 2.60(m, 4H), 2.17 (t, CH2).

EXAMPLE 23

2-{3-[4-(1H-Indol-3-yl)-piperidin-1-yl]-propyl}-2H-[1,2,4]triazolo[4,3-a]pyridin-3-one

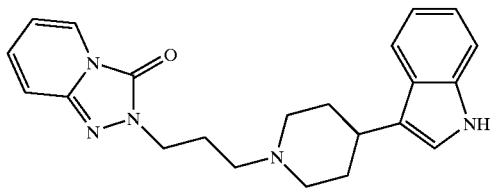

2-{3-[4-(1H-Indol-3-yl)-piperidin-1-yl]-propyl}-2H-[1,2,4]triazolo[4,3-a]pyridin-3-one was prepared in a similar fashion to compound 22, using 2-(3-Chloro-propyl)-2H-[1,2,4]triazolo[4,3-a]pyridin-3-one and 3-Piperidin-4-yl-1H-indole. Yield: 90 mg (48%); mp: 111.7° C. M+: 376.1; (300 MHz, CDCl$_3$): 8.04 (s, 1H, NH), 7.77 (d, 1H), 7.62(d, 1H), 7.35(d, 1H), 7.09(m, 5H), 6.59(m, 1H), 6.49 (m, 1H), 4.08 (m, CH2), 3.10 (d, CH2), 2.70 (t, CH) 2.55(t, CH2), 2.04(m, 4H), 1.82(m, CH2).

EXAMPLE 24

2-{2-[4-(1H-Indol-3-yl)-3,6-dihydro-2H-pyridin-1-yl]-ethyl}-2H-[1,2,4]triazolo[4,3-a]pyridin-3-one

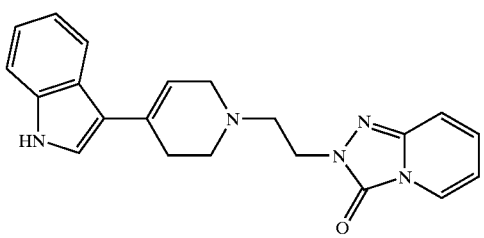

Toluene-4-sulfonic acid 2-(3-oxo-[1,2,4]triazolo[4,3-a]pyridin-2-yl)-ethyl ester was prepared starting from 1,2,4-triazolo pyridinone. 1,2,4-triazolo pyridinone (1.485 g, 10 mmol) was dissolved in 220 ml acetone. The solution under nitrogen was then added 17 gram potassium carbonate and 1.364 bromoethanol(1.1 eq). The mixture was refluxed under nitrogen for 18 hours. It was then cooled down to room temperature and poured into about 300 ml water and extracted with ethyl acetate (2×20 ml). The combined organic layers were dried over magnesium sulfate and filtered and concentrated. Flash column chromatography using 1:1 mixture of hexane and ethyl acetate yielded 2.5 gram crude product. The crude compound was dissolved in a 1:1 mixture of THF/DMF. The solution was put under nitrogen and added 800 mg NaH(60%, 20 mmol). The mixture was stirred under nitrogen for half an hour. Tosyl chloride 2.1 gram (11 mmol, 1 eq) was next added to the reaction media and the resulting solution was heated at 50° C. for 18 hours. Then it was cooled down to room temperature and methanol was added under nitrogen until no bubbles observed. It was then poured into about 300 ml water and extracted with ethyl acetate (2×200 ml). The combined organic layers were dried over magnesium sulfate and filtered and concentrated. Flash column chromatography using 70% ethyl acetate/hexane and yielded 834 mg of product (23%).

Toluene-4-sulfonic acid 2-(3-oxo-[1,2,4]triazolo[4,3-a]pyridin-2-yl)-ethyl ester 166 mg (0.5 mmol) was dissolved in 50 ml DMSO. To this solution was added 99 mg of 3-(1,2,3,6-Tetrahydro-pyridin-4-yl)-1H-indole, (1 eq, 0.5 mmol) and 5 ml triethyl amine. The reaction media was heated under nitrogen at 85° C. for 18 hours. It was then cooled down to room temperature and poured into about 300 ml water and extracted with ethyl acetate (2×200 ml). The combined organic layers were dried over magnesium sulfate and filtered and concentrated. Flash column chromatography using ethyl acetate and 20% methanol/ethyl acetate yielded 54 mg product (30%). mp: 170.4° C.; M+: 360.1; H-NMR: 8.28 (b, 1H, NH), 7.88 (d, 1H), 7.55(d, 1H), 7.30(d, 1H), 7.14(m, 5H), 6.47(m, 1H), 6.19 (m, 1H), 4.25 (m, CH2), 3.35 (d, CH2), 3.00 (t, CH2) 2.86 (t, CH2), 2.60(m, CH2).

EXAMPLE 25

2-{2-[4-(1H-Indol-3-yl)-piperidin-1-yl]-ethyl}-2H-[1,2,4]triazolo[4,3-a]pyridin-3-one

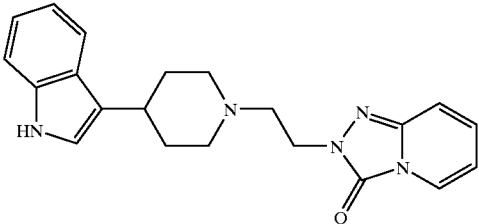

2-{2-[4-(1H-Indol-3-yl)-piperidin-1-yl]-ethyl}-2H-[1,2,4]triazolo[4,3-a]pyridin-3-one was prepared in a similar fashion to of 2-{2-[4-(1H-Indol-3-yl)-3,6-dihydro-2H-pyridin-1-yl]-ethyl}-2H-[1,2,4]triazolo[4,3-a]pyridin-3-one (example 22) using of toluene-4-sulfonic acid 2-(3-oxo-[1,2,4]triazolo[4,3-a]pyridin-2-yl)-ethyl ester and 3-Piperidin-4-yl-1H-indole. Yield: 70 mg of compound was obtained (39%). mp: 142° C.; M+: 362.1; H-NMR: 8.14 (b, 1H, NH), 7.74 (m, 1H), 7.62 (m, 1H), 7.35(m, 1H), 7.08 (m, 5H), 6.94 (m, 1H), 6.45 (m, 1H), 4.23 (m, CH2), 3.13 (d, CH2), 2.93 (m, CH2), 2.82 (m, 1H) 2.28 (t, CH2), 2.04(m, CH2), 1.86(m, CH2).

EXAMPLE 26

2-{4-[4-(1H-Indol-3-yl)-3,6-dihydro-2H-pyridin-1-yl]-butyl}-2H-[1,2,4]triazolo[4,3-a]pyridin-3-one

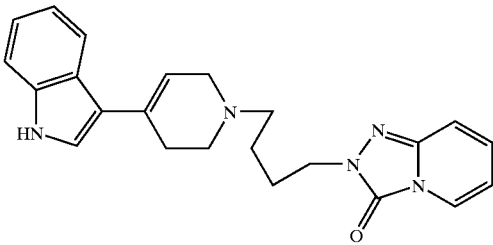

2-{4-[4-(1H-Indol-3-yl)-3,6-dihydro-2H-pyridin-1-yl]-butyl}-2H-[1,2,4]triazolo[4,3-a]pyridin-3-one was prepared by reacting 2-(4-Chloro-butyl)-2H-[1,2,4]triazolo[4,3-a]pyridin-3-one (225 mg, 1 mmol) and 3-(1,2,3,6-Tetrahydro-pyridin-4-yl)-1H-indole (198 mg, 1 mmol) by adopting the procedure as outlined in Experimental 24. Yield: 87 mg (22%) compound was isolated as pale yellow solid.

Mp: 123.2° C.; M+388.1
H-NMR (d6-DMSO): 11.20 (b, 1H, NH), 7.85 (m, 1H), 7.79 (m, 1H), 7.35 (m, 2H), 7.23(m, 2H), 7.09 (m, 1H), 7.01 (m, 1H), 6.61 (m, 1H), 6.10 (m, 1H), 3.94 (m, CH2), 3.07 (m, CH2), 2.59 (m, CH2), 2.50 (m, 4H), 2.41 (m, CH2) 1.80 (m, CH2), 1.69 (m, CH2), 1.48 0(m, CH2).

EXAMPLE 27

The 5-HT transporter affinity of the compounds of this invention was established in accordance with standard pharmaceutically accepted test procedures with representative compounds as follows:

Rat Brain $^3$H-Paroxetine Binding Assay (RB 5HT Transporter):

This assay was used to determine a compound's affinity of the 5-HT transporter.

A protocol similar to that used by Cheetham et. al. (Neuropharmacol. 1993, 32, 737) was used. Briefly, frontal cortical membranes prepared from male S.D. rats were incubated with $^3$H-parxetine (0.1 nM) for 60 min. at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to $K_i$ values using the method of Cheng and Prusoff (Biochem. Pharmacol. 1973, 22, 3099);

$$K_i = \frac{IC_{50}}{\text{Radioligand concentration}/1 + KD)}$$

Inhibition of $^3$H-5-HT Uptake by Cells Possessing the Human 5-HT Transporter (HC 5HT Transporter):

A human carcinoma cell line (Jar cells) possessing low endogenous levels of the 5-HT-transporter are seeded into 96 well plates and treated with staurosporine at least 18 h prior to assay. [Staurosporine greatly increases the expression of the 5-HT-transporter.] On the day of assay, vehicle, excess of fluoxetine, or test compound is added to various wells on the plate. All wells then receive $^3$H-5-HT and are incubated at 37° C. for 5 min. The wells are then washed with ice cold 50 mM Tris HCl (pH 7.4) buffer and aspirated to remove free $^3$H-5-HT. 25 μl of 0.25 M NaOH is then added to each well to lyse the cells and 75 μl scintillation cocktail (Microscint™ 20) added prior to quantitation on a Packard TopCount machine. Tubes with vehicle represent total possible uptake, radioactivity counted in tubes with fluoxetine represent nonspecific binding/uptake and is subtracted from the total possible uptake to give total possible specific uptake. This nonspecific binding (usual low in number) is then subtracted from the counts obtained in wells with various test compounds (or different concentrations of test drug) to give specific uptake in the presence of drug. Specific uptake is then expressed as a % of control values and is analyzed using nonlinear regression analysis (Prizm) to determine $IC_{50}$ values. If the compound is active at inhibiting 5-HT uptake, its counts will be close to that obtained with fluoxetine.

High affinity for the serotonin $5-HT_{1A}$ receptor was established by testing the claimed compound's ability to displace [$^3$H] 8-OH-DPAT (dipropylaminotetralin) from the $5-HT_{1A}$ serotonin receptor following a modification of the procedure of Hall et al., J. Neurochem. 44, 1685 (1985) which utilizes CHO cells stably transfected with human $5-HT_{1A}$ receptors. The $5-HT_{1A}$ affinities for the compounds of the invention are reported below as $K_i$'s.

Antagonist activity at $5-HT_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human. $5-HT_{1A}$ receptors was determined. Agonists produce an increase in binding whereas antagonists produce no increase but rather reverse the effects of the standard agonist 8-OH-DPAT. The test compound's maximum inhibitory effect is represented as the $I_{max}$, while its potency is defined by the $IC_{50}$.

Results from these two assays are presented below in Table I.

TABLE I

| Compound | 5-HT1A $K_i$ (nM) | RB 5HT Transporter $K_i$ (nM) | HC 5HT Transporter $IC_{50}$ (nM) |
|---|---|---|---|
| Example 1 | 83.82 | 2.87 | 125 |
| Example 2 | 72.1 | 36 | 273 |
| Example 3 | 82.2 | 4.57 | NT |
| Example 4 | 215 | 1.25 | 132 |
| Example 5 | 86.81 | 4.12 | 55.3 |
| Example 6 | 285.65 | 0.80 | 43.2 |
| Example 7 | 200.8 | 11 | 173 |
| Example 8 | 31% @ 1000 nM | 1.92 | NT |
| Example 9 | 4% @ 1000 nM | 0.31 | NT |
| Example 10 | 7% @ 1000 nM | 1.14 | 268 |
| Example 11 | 26% @ 1000 nM | 40 | 1910 |
| Example 12 | 38.16 | 5.5 | 88.1 |
| Example 13 | 42% @ 1000 nM | 37 | 651 |
| Example 14 | 43% @ 1000 nM | 116 | 1480 |
| Example 15 | 44% @ 1000 nM | 19 | 159 |
| Example 16 | 56.72 | 3.52 | 37.5 |
| Example 17 | 118.75 | 16 | 190 |
| Example 18 | 80.86 | 21 | 231 |
| Example 19 | 315.35 | 0.15 | 15.7 |
| Example 20 | 49% @ 1000 nM | 10 | NT |
| Example 21 | 630.55 | 0.56 | NT |

Hence the compounds of this invention have substantial affinity for the 5-HT transporter & 5 $HT_{1A}$ receptors and are useful in the treatment of diseases affected by disorders of the serotonin affected neurological systems, such as depression and anxiety, by administration orally, parenterally, or by aspiration to a patient in need thereof.

Many variations of the present invention not illustrated herein will occur to those skilled in the art. The present invention is not limited to the embodiments illustrated and described herein, but encompasses all the subject matter within the scope of the appended claims

What is claimed is:

1. A compound represented by the formula I:

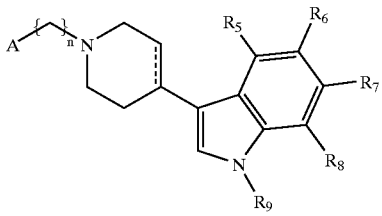

wherein A represents the following heterocycles:

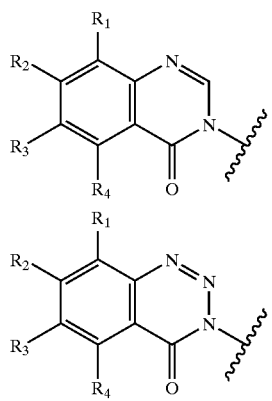

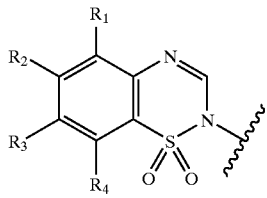

n is 2 to 4;

$R_1$, $R_2$, $R_3$, $R_4$, $R_5$, $R_6$, $R_7$ and $R_8$ are each independently hydrogen, straight chain alkyl of 1 to 4 carbon atoms, branched chain alkyl of 3 to 6 carbon atoms, cycloalkyl of 3 to 10 carbon atoms, halogen, alkoxy group of 1 to 4 carbon atoms, heteroaryloxy, cycloalkoxy having 3 to 6 ring members, heterocycloalkoxy of 3 to 6 ring members selected from C, O, S and N where N may have a substituent $R_9$, hydroxy, nitro, nitrile, amino, carboxy, alkoxycarbonyl of 1 to 4 carbon atoms, alkylcarbonyl of 1 to 4 carbon atoms, aminocarbonyl and alkylaminocarbonyl of 1 to 12 carbon atoms, straight or branched chain fluorinated alkyl of 1 to 4 carbon atoms, aryl, aryloxy, alkylaryl of 7 to 12 carbon atoms, heteroaryl, heterocycloalkyl having ring atoms selected from atom C, S, O and N where N may have a substituent $R_9$;

$R_9$ is $C_1$–$C_6$ alkyl optionally substituted with $R_{10}$, $C_3$-$C_6$ alkenyl or alkynyl with the proviso that a carbon bearing a double or triple bond is not bonded directly to a ring heteroatom, $C_6$–$C_{10}$ aryl optionally substituted with $R_{10}$, $C_7$-$C_{12}$ alkylaryl optionally substituted with $R_{10}$, heteroaryl optionally substituted with $R_{10}$, alkylheteroaryl optionally substituted with $R_{10}$, $SO_2$-aryl, or $SO_2$-alkyl;

$R_{10}$ is halogen, nitrile, alkoxy, aryloxy, aryl, heteroaryl, cycloalkyl, or heterocycloalkyl with a hetero atom selected from N, O and S, and each crystalline form and pharmaceutically acceptable salt thereof.

2. A compound according to claim 1 selected from the group consisting of:

3-[2-(4-(1H-indol-3-yl)-3,6-dihydro-1(2H)-pyridinyl)ethyl]-6-7-dimethoxy-4(3H)-quinazolinone;

3-[2-(4-(1H-indol-3-yl)-1-piperidinyl)ethyl]-6-7-dimethoxy-4(3H)-quinazolinone;

3-[2-(4-(5-fluoro-1H-indol-3-yl)-3,6-dihydro-1(2H)-pyridinyl)ethyl]-6-7-dimethoxy-4(3H)-quinazolinone;

3-[4-(4-(1H-indol-3-yl)-3,6-dihydro-1(2H)-pyridinyl)butyl]-6-7-dimethoxy-4(3H)-quinazolinone;

3-[4-(4-(1H-indol-3-yl)-1-piperdinyl)butyl]-6-7-dimethoxy-4(3H)-quinazolinone;

3-[3-(4-(1H-indol-3-yl)-3,6-dihydro-1(2H)-pyridinyl)propyl]-6-7-dimethoxy-4(3H)-quinazolinone;

3-[3-(4-(1H-indol-3-yl)-1-piperidinyl)propyl]-6-7-dimethoxy-4(3H)-quinazolinone;

3-[3-(4-(5-fluoro-1H-indol-3-yl)-3,6-dihydro-1(2H)-pyridinyl)propyl]-6-7-dimethoxy-4(3H)-quinazolinone;

8-bromo-6-chloro-3-[3-(4-(5-(1H-indol-3-yl)-3,6-dihydro-1(2H)-pyridinyl)propyl]-4(3H)-quinazolinone}-quinoline;

6-Chloro-3-[3-(4-(1H-indol-3-yl)-3,6-dihydro-1(2H)-pyridinyl)propyl]-4(3H)-quinazolinone;

6-Chloro-3-[2-(4-(1H-indol-3-yl)-piperidinyl)propyl]-4(3H)-quinazolinone;

3-[2-(4-(1H-indol-3-yl)-3,6-dihydro-1(2H)-pyridinyl) ethyl]-4(3H)-quinazolinone;

3-[2-(4-(1H-indol-3-yl)-1-piperidinyl)ethyl]-4(3H)-quinazolinone;

3-[2-(4-(1-methyl-1H-indol-3-yl)-1-piperidinyl)ethyl]-4-(3H)-quinazolinone;

6-Fluoro-3-[2-(4-(1H-indol-3-yl)-3,6-dihydro-1(2H)-pyridinyl)ethyl]-4(3H)-quinazolinone;

3-[2-(4-(1H-indol-3-yl)-3,6-dihydro-1(2H)-pyridinyl) ethyl]-1,2,3-benzotriazin-4(3H)-one;

3-[2-(4-(1H-indol-3-yl)-1-piperidinyl)ethyl]-1,2,3-benzotriazin-4(3H)-one;

3-[2-(4-(1-methyl-1H-indol-3-yl)-1-piperidinyl)ethyl]-1,2,3-benzotriazin-4(3H)-one;

3-[2-(4-(1H-indol-3-yl)-3,6-dihydro-1(2H)-pyridinyl) propyl]-1,2,3-benzotriazin-4(3H)-one;

3-[2-{4-(1H-indol-3-yl)-1-piperidinyl)propyl]-1,2,3-benzotriazin-4(3H)-one;

3-[2-(4-(1-methyl-1H-indol-3-yl)-1-piperidinyl)propyl]-1,2,3-benzotriazin-4(3H)-one, or a pharmaceutically acceptable salt of said compound.

3. A composition comprising a compound according to claim 2 and a pharmaceutically acceptable carrier.

4. A composition comprising a compound according to claim 1 and a pharmaceutically acceptable carrier.

5. A method for treating depression or anxiety in a human in need thereof, said method comprising administering to said human a therapeutically effective amount of a compound of claim 1.

* * * * *